United States Patent [19]

Käsbauer et al.

[11] Patent Number: 4,827,057

[45] Date of Patent: May 2, 1989

[54] PROCESS FOR PREPARING 1,2-DICHLOROBENZENE

[75] Inventors: Josef Käsbauer, Wermelskirchen; Helmut Fiege; Herbert Schmidt, both of Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 219,109

[22] Filed: Jul. 14, 1988

[30] Foreign Application Priority Data

Jul. 30, 1987 [DE] Fed. Rep. of Germany ....... 3725196

[51] Int. Cl.$^4$ ...................... C07C 17/00; C07C 25/08
[52] U.S. Cl. .................................................. 570/204
[58] Field of Search ......................................... 570/204

[56] References Cited

U.S. PATENT DOCUMENTS

| 2,866,828 | 12/1958 | Crowder et al. | 570/204 |
| 2,886,605 | 5/1959 | McClure et al. | 570/204 |
| 2,943,114 | 6/1960 | Redman et al. | 570/204 |
| 2,949,491 | 8/1960 | Rucker | 570/204 |
| 3,595,931 | 7/1971 | Hay et al. | 570/204 |

Primary Examiner—Werren B. Lone
Attorney, Agent, or Firm—Sprung Horn Kramer & Woods

[57] ABSTRACT 1,2-Dichlorobenzene can be prepared by reacting 1,2,4-trichlorobenzene in the gas phase with hydrogen. The reaction is carried out at a temperature from the boiling point of the starting material up to about 400° C. and over a platinum-spinel catalyst.

17 Claims, No Drawings

PROCESS FOR PREPARING 1,2-DICHLOROBENZENE

BACKGROUND OF THE INVENTION

The present invention relates to a process for the catalytic dehydrohalogenation of 1,2,4,-trichlorobenzene with hydrogen to form 1,2-dichlorobenzene over a platinum-spinel catalyst.

U.S. Pat. No. 2,866,828 discloses the dehalogenation of trihalogenated benzenes over various catalysts, aiming predominantly at the 1,3-dihalobenzene. In Example 4 of this U.S. Patent, a 1,2,4-trisubstituted benzene is dehalogenated over a platinum-charcoal catalyst. However, in this reaction, the industrially unimportant, 1,2,4-tribromobenzene is used in only one short test run; in addition, a high percentage of monobromobenzene is formed.

U.S. Pat. No. 2,943,114 likewise describes the preparation of m-dichlorobenzene by reference to short test runs. Using various catalysts, only low selectivity of dehalogenation is observed on the whole. In Example 5 of this U.S. Patent, a platinum/aluminium oxide catalyst in used without the experimental results being reported.

In U.S. Pat. No. 3,595,931, complete dehalogenation which, according to Example 5 of this U.S. Patent, achieves a 70% conversion is aimed at by means of a platinum/aluminium oxide catalyst doped with potassium hydroxide.

U.S. Pat. No. 2,886,605 describes the dehalogenation of aliphatic and aromatic halogen compounds. The reaction is carried out in a fluidized bed over an aluminium oxide/cuprous chloride catalyst. According to the short test runs described only a small amount of dichlorobenzenes, whose main component is the m-isomer, are obtained in the reaction mixture.

However, to carry out a dehydrohalogenation from industrial aspects, a high selectivity of the process and a long catalyst life in combination with almost undiminished activity are desired. Surprisingly, it has now been found that in this respect the selection of spinels as carriers plays a dominant role. Such catalysts used according to the invention show only a small degree of deactivation even in long-term experiments of over 2,000 hours.

SUMMARY OF THE INVENTION

A process for preparing 1,2-dichlorobenzene has been found which is characterized in that 1,2,4-trichlorobenzene is reacted as the starting material in the gas phase at a temperature from the boiling point of the starting material up to 400° C. with hydrogen over a platinum/spinel catalyst.

DETAILED DESCRIPTION OF THE INVENTION 1,2,4-Trichlorobenzene can, for example, be obtained by chlorination of 1,4-dichlorobenzene in a manner known to a person skilled in the art.

According to the invention, 1,2,4-trichlorobenzene can also be used as a mixture with other polychlorobenzenes. The term other polychlorobenzenes is to be understood as meaning other trichlorobenzenes and tetrachlorobenzenes, preferably 1,2,3-trichlorobenzene, 1,2,3,4-tetrachlorobenzene and 1,2,4,5-tetrachlorobenzene and 1,2,4,5-tetrachlorobenzene. Even minor amounts of dichlorobenzenes, in particular the desired 1,2-dichlorobenzene, can be present in the starting material in addition to 1,2,4-trichlorobenzene. This broad applicability of the process according to the invention even to industrial chlorination mixtures is particularly advantageous. In particular, a chlorination mixture containing 1,2,4-trichlorobenzene which originated from the chlorination of 1,4-dichlorobenzene can be used without it being necessary that such a mixture be worked up to obtain pure 1,2,4-trichlorobenzene.

According to the invention, platinum/spinel catalysts are used. The amount of platinum present in these catalysts is 0.1 to 5% by weight, preferably 0.5-2% by weight, based on the total weight of the catalyst. A higher platinum concentration is of no further advantage. The carrier of the catalyst is a spinel. Suitable spinel-forming elements are for example Li, Be, Mg, Ln, Mn, Cu, Ni, besides the aluminum. LiAl spinel may be mentioned particularly as a carrier material.

It has further been found that the catalyst described is further improved for the process according to the invention if it is additionally doped with an alkaline earth metal (hydr)oxide. The alkaline earth metals can be Mg, Ca, Sr or Ba, and also mixtures thereof. Preference is given to doping with magnesium (hydr)oxide. The amount of such doping present is 0.01 to 10% by weight, preferably 0.1 to 5% by weight, based on the total weight of the catalyst.

The catalyst to be used according to the invention is prepared by soaking a commercial spinel, for example a LiAl spinel, in an aqueous platinum salt solution and treating it with a base (sodium hydroxide solution, potassium hydroxide solution, sodium carbonate solution, potassium carbonate solution inter alia) and a reducing agent (hydrazine hydrate, formic acid, formaldehyde inter alia) to precipitate metallic platinum. Such a catalyst is subsequently washed and dried at elevated temperature, for example 300° to 500° C. This drying process can be advantageously carried out in the reaction apparatus which is planned to be used for the dehydrohalogenation according to the invention, before the starting material and the hydrogen are added. Where the catalyst to be used according to the invention is additionally to be doped with an alkaline earth metal (hydr)oxide, the spinel is soaked in a suitable alkaline earth metal salt solution (for example a chloride or a nitrate), advantageously together with the platinum salt solution. In a manner known to the person skilled in the art, the amount and concentration of the solution containing the platinum and the alkaline earth metal salt is selected in such a way that the desired final concentration is reached. During the treatment with a base, the alkaline earth metal is then precipitated in the form of its hydroxide. It may be assumed that during the drying within the temperature range given the alkaline earth metal hydroxide is partially converted into the alkaline earth metal oxide.

The dehydrohalogenation (dehalogenation) is carried out in the gas phase using any desired reaction apparatuses suitable for this reaction. The temperature of the process according to the invention can be selected to range from the boiling point of the starting material up to 400° C., preferably from 250° to 350° C.

The reaction can be carried out not only at atmospheric pressure but also at superatmospheric pressure, for example up to 10 bars, the temperature being adjusted such that the starting material is present in the gas phase.

The amount of hydrogen used is 0.5 to 5 mol, preferably 0.9 to 2 mol per equivalent of chlorine to be removed. In this manner, the desired amount to be converted in the process according to the invention can be selected. Preferably, hydrogen is used in excess.

EXAMPLE 1

LiAl spinel was soaked in an aqueous platinum salt solution, treated with sodium hydroxide solution and hydrazine hydrate and subsequently washed. 35 ml of catalyst having a grain size of 1.5 to 2.5 mm were dried and dehydrated in a heatable glass or metal tube at 300° to 500° C. The catalyst contained 1% by weight of Pt, based on its total weight.

At 300° C., 19 ml of 1,2,4-trichlorobenzene per hour were evaporated off and reacted as a gas over the catalyst with 4 l of $H_2$/h. The product mixture was condensed and tested by gas chromatography. From the long-term experiment, three exemplary compositions are listed.

| Substance [%] | time on stream [h] | | |
| --- | --- | --- | --- |
| | 52 | 221 | 841 |
| Benzene | 7.6 | 4.0 | 3.2 |
| Chlorobenzene | 5.1 | 5.3 | 6.1 |
| 1,2-Dichlorobenzene | 27.6 | 26.5 | 25.1 |
| 1,3-Dichlorobenzene | 4.9 | 4.9 | 4.9 |
| 1,4-Dichlorobenzene | 1.7 | 2.3 | 2.5 |
| 1,2,4-Trichlorobenzene | 53.0 | 56.9 | 57.9 |

The catalyst was not regenerated during the entire reaction time.

EXAMPLE 2

The same catalyst as in Example 1, but additionally doped with 1% of MgO, was used in a long-term experiment at 300° C. An hourly flow rate of 19 ml of 1,2,4-trichlorobenzene and 4 l of $H_2$ gave, after 97 hours of operation, the product mixture listed in the Table (1st column).

The numbers in the second column refer to a flow rate of 35 ml of 1,2,4-trichlorobenzene per hour after 100 hours of operation. This experiment ran for about 1000 hours without regeneration of the catalyst, whose activity remained unchanged.

| | 97 h at 19 ml/h | 100 h at 35 ml/h |
| --- | --- | --- |
| Benzene | 4.3% | 1.6% |
| Chlorobenzene | 12.9% | 5.9% |
| 1,2-Dichlorobenzene | 36.5% | 22.4% |
| 1,3-Dichlorobenzene | 6.7% | 4.9% |
| 1,4-Dichlorobenzene | 3.8% | 3.2% |
| 1,2,4-Trichlorobenzene | 35.8% | 59.0% |

EXAMPLE 3

The same catalyst as in Example 2 was used in a pressure tube at 4 bar/300° C. 60 ml of 1,2,4-trichlorobenzene and 10.8 l of $H_2$ per hour were reacted over 30 ml of catalyst. During a long-term experiment, the following representative spectrum of products was obtained after 101 hours:

| Benzene | 2.6 |
| --- | --- |
| Chlorobenzene | 8.1 |
| 1,2-Dichlorobenzene | 26.0 |
| 1,3-Dichlorobenzene | 5.6 |
| 1,4-Dichlorobenzene | 3.7 |
| 1,2,4-Trichlorobenzene | 54.0 |

The experiment ran for 1500 hours without regeneration of the catalyst, whose activity and selectivity remained almost unchanged.

EXAMPLES 4–6

(Comparison examples)

In comparison with Examples 1 and 2, 1% of Pt was applied to other carrier materials and tested under the same conditions. The following table shows the conversion after 50 and 100 hours in a long-term experiment.

| Example | Carrier material | Conversion (%) after | | |
| --- | --- | --- | --- | --- |
| | | 50 h | 100 h | |
| 4 | $SiO_2$ | 13 ± 1 | 9 ± 1 | Comparison example |
| 5 | Charcoal | 15 ± 1 | 11 ± 1 | Comparison example |
| 6 | $Al_2O_3$ | 21 ± 1 | 16 ± 3 | Comparison example |
| 1 | LiAl spinel | 45 ± 3 | 38 ± 3 | |
| 2 | MgO/LiAl spinel | 62 ± 3 | 61 ± 4 | |
| (Column 1) | | | | |

EXAMPLE 7

Under the conditions of Example 2, 19 ml of a mixture containing 7% of 1,2-dichlorobenzene, 77% of 1,2,4-trichlorobenzene and 15% of 1,2,3-trichlorobenzene were reacted per hour. After a reaction time of 111 hours, the following representative product mixture was analysed:

| Benzene | 1.6% |
| --- | --- |
| Chlorobenzene | 6.9% |
| 1,2-Dichlorobenzene | 34.9% |
| 1,3-Dichlorobenzene | 4.5% |
| 1,4-Dichlorobenzene | 2.2% |
| 1,2,4-Trichlorobenzene | 39.7% |
| 1,2,3-Trichlorobenzene | 10.2% |

EXAMPLE 8

A mixture of 80% of 1,2,4-trichlorobenzene, 12% of 1,2,4,5-tetrachlorobenzene and 8% of 1,2,3,4-tetrachlorobenzene was reacted at 300° C. over 1% Pt/1% MgO/1% KOH/LiAl spinel with 4 l of $H_2$/h. After 20 hours, the following product mixture was obtained:

| Benzene | 1.8% |
| --- | --- |
| Chlorobenzene | 8.6% |
| 1,2-Dichlorobenzene | 30.7% |
| 1,3-Dichlorobenzene | 6.0% |
| 1,4-Dichlorobenzene | 3.4% |
| 1,2,4-Trichlorobenzene | 38.6% |
| 1,2,3-Trichlorobenzene | 3.1% |
| 1,2,4,5-Tetrachlorobenzene | 4.9% |
| 1,2,3,4-Tetrachlorobenzene | 2.9% |

What is claimed is:

1. A process for preparing 1,2-dichlorobenzene, characterized in that 1,2,4-trichlorobenzene is reacted as the starting material in the gas phase at a temperature from the boiling point of the starting material up to 400° C. with hydrogen over a platinum/spinel catalyst.

2. A process according to claim 1, characterized in that 1,2,4-trichlorobenzene is used as a mixture with other polychlorobenzenes.

3. A process according to claim 2, characterized in that the polychlorobenzenes used are those from the group consisting of 1,2,3-trichlorobenzene, 1,2,3,4-tetrachlorobenzene and 1,2,4,5-tetrachlorobenzene.

4. A process according to claim 2, characterized in that a mixture containing 1,2,4-trichlorobenzene is used which originated from industrial chlorination mixtures.

5. A process according to claim 4, characterized in that a mixture is used which originated from the chlorination of 1,4-dichlorobenzene.

6. A process according to claim 1, characterized in that it is carried out at 250° to 350° C.

7. A process according to claim 1, characterized in that 0.5 to 5 moles of hydrogen are used per equivalent of chlorine to be removed.

8. A process according to claim 7, characterized in that 0.9 to 2 moles of hydrogen are used per equivalent of chlorine to be removed.

9. A process according to claim 1, characterized in that the spinel is formed, besides the aluminum, by one or more elements of the group Li, Be, Mg, Zn, Mn Cu and Ni.

10. A process according to claim 9, characterized in that the catalyst carrier is LiAl spinel.

11. A process according to claim 1, characterized in that the catalyst contains 0.1 to 5% by weight of platinum, based on its total weight.

12. A process according to claim 11, characterized in that the catalyst contains 0.5-2% by weight of platinum.

13. A process according to claim 1, characterized in that the catalyst is doped with an alkaline earth metal (hydr)oxide or with a mixture of alkaline earth metal (hydr)oxides.

14. A process according to claim 13, characterized in that the catalyst is doped with magnesium (hydr)oxide.

15. A process according to claim 13, characterized in that the alkaline earth metal (hydr)oxide is present in an amount of 0.01-10% by weight, based on the total weight of the catalyst.

16. A process according to claim 15, characterized in that the alkaline earth metal (hydr)oxide is present in an amount of 0.1-5% by weight, based on the total weight of the catalyst.

17. A process according to claim 1, characterized in that it is carried out at a pressure of from 1 to 10 bars.

* * * * *

UNITED STATES PATENT AND TRADEMARK OFFICE
CERTIFICATE OF CORRECTION

PATENT NO. : 4,827,057
DATED : May 2, 1989
INVENTOR(S) : Käsbauer et al.

It is certified that error appears in the above-identified patent and that said Letters Patent is hereby corrected as shown below:

Col. 2, line 15            Delete "Ln" and substitute --Zn--

Signed and Sealed this

Thirty-first Day of July, 1990

Attest:

HARRY F. MANBECK, JR.

*Attesting Officer*        *Commissioner of Patents and Trademarks*